United States Patent [19]
deGroot et al.

[11] Patent Number: 6,046,809
[45] Date of Patent: Apr. 4, 2000

[54] REAL-TIME IN SITU MULTIPLE GAS SPECIES SENSING METHOD

[75] Inventors: Wilhemus A. deGroot, Rocky River; Joseph A. Powell, Akron, both of Ohio

[73] Assignee: S3 Incorporated, Akron, Ohio

[21] Appl. No.: 09/018,750

[22] Filed: Feb. 4, 1998

[51] Int. Cl.$^7$ .................................................. G01N 21/00
[52] U.S. Cl. .......................................... 356/337; 356/338
[58] Field of Search .................................... 356/337, 339, 356/338, 335, 336, 340, 342; 250/373, 343, 435; 436/156, 91, 94, 155, 159

[56] References Cited

U.S. PATENT DOCUMENTS 5,789,256  8/1998  Marlow et al. ........................ 436/156

Primary Examiner—Frank G. Font
Assistant Examiner—Tu T. Nguyen
Attorney, Agent, or Firm—Oldham & Oldham Co., LPA

[57] ABSTRACT

A method for sensing the concentrations of diatomic gases in a flow chamber is achieved by focusing an incident beam of light from a monochromatic light source on a point internal to the flow chamber through a transparent window. The incident excites molecules of the diatomic gas, resulting in emission of scattered light of particular characteristic frequency for each species of diatomic gas, due to the Raman principle. By collecting the scattered light beam from the flow chamber through the window and analyzing the intensity of the collected scattered beam at these characteristic frequencies, the relative concentrations of each of the diatomic gases may be determined.

14 Claims, 3 Drawing Sheets

REAL-TIME IN SITU MULTIPLE GAS SPECIES SENSING METHOD

The present invention relates to a device for sensing multiple gas species to provide real-time in situ determination of the operation of important processes, including heat treating furnaces. Once these data are obtainable, real time control of the process becomes feasible.

BACKGROUND OF THE ART

Prior methods do not permit real-time in situ detection and analysis of the various gas species present in a heat treating furnace. This inability to detect and analyze results in an inability to precisely control, resulting in waste of energy and materials and needless pollution. A variety of prior art techniques take off a slip stream of the gas for analysis. Such slip stream analyses require that the gas sample be cooled, possibly resulting in changes in the gas composition. Further, the time inherently involved in isolating and cooling the gas sample results in a time lag, which prevents real time in-situ analysis.

SUMMARY OF THE INVENTION

It is therefore, desired to provide a method for detecting multiple gas species in a combustion operation and to provide data in a real-time manner for controlling important process variables. Such a method comprises the steps of: a) providing the flow chamber with a window transparent to light in the visible spectrum; b) focusing an incident beam from a monochromatic light source on a point internal to the flow chamber through the window; c) collecting a scattered light beam from the flow chamber passing external to the flow chamber through the window; and d) analyzing the intensity of the collected scattered beam in at least one characteristic frequency for each of the at least one diatomic gases. It is preferred to bring the incident beam proximate to the window in a first fiber optic cable and to collect the scattered beam proximate to the window in a second fiber optic cable. The method may be conducted when temperatures at the focal point of the incident beam are in excess of 250°0 F., and more particularly, in excess of 1000° F.

The preferred monochromatic light source is an argon ion laser with a wavelength of 514.5 nm. The preferred diatomic gas for being sensed with this method is a mixture primarily including carbon monoxide, hydrogen and nitrogen, with small amounts of oxygen being also capable of being sensed.

BRIEF DESCRIPTION OF THE DRAWINGS

Better understanding of the present invention will be had when reference is made to the accompanying drawings, wherein identical parts are identified by identical reference numerals and wherein.

DETAILED DESCRIPTION OF THE PREFERRED EMBODIMENTS

Figure 1:
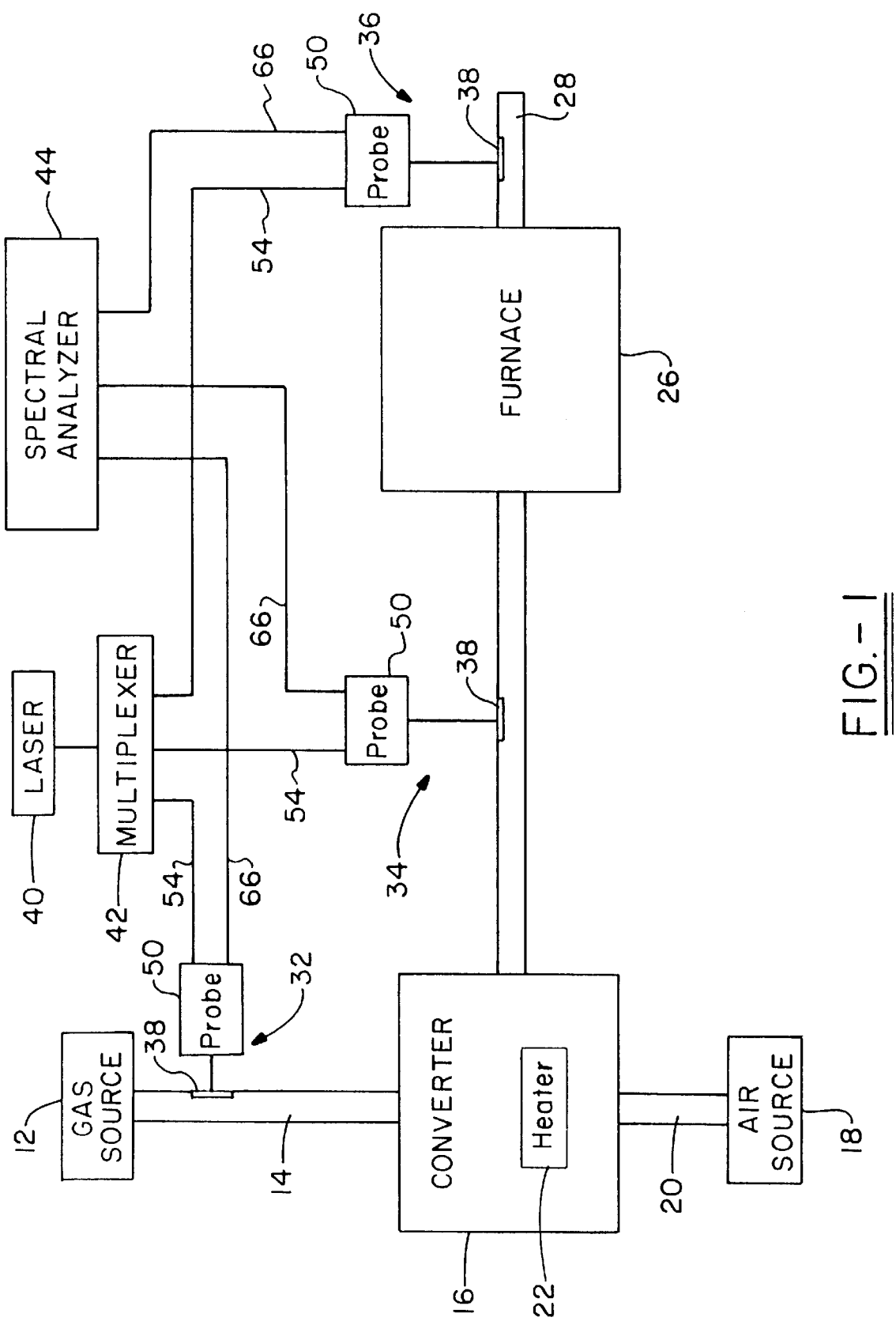
FIG. 1 shows a schematic of the system employing the present invention method.

The carbon potential of a carrier gas, particularly as used in a heat treating furnace in the heat treating industry, is defined as the degree to which a protective atmosphere provides carbon for absorption. The carbon potential varies upon the composition of the gas and the furnace temperature. Many heat treating operations use an endothermic gas composition as a protective atmosphere. Such a gas comprises about 20% carbon monoxide (CO), about 40% nitrogen ($N_2$), and about 40% hydrogen ($H_2$). The gas may also contain small amounts of hydrocarbons or air to adjust the carbon potential upwardly or downwardly. The quality of the finished product of a heat treating furnace will depend upon the composition of the endothermic gas used.

The endothermic gas used in the furnace is generated in large part by passing a hydrocarbon such as natural gas mixed with air over a heated catalytic surface. The combination of temperature and catalytic action result in the endothermic gas being produced. A number of variables affect the quality of the resultant endothermic gas, including composition of the natural gas used, the gas/air volumetric ratio, temperature, residence time over the catalyst, and catalyst bed condition.

It is important to monitor the carbon potential of the endothermic gas. Temperature, dewpoint and carbon potential are directly related, so if one knows any two of the variables, the third may be inferred. However, an accurate in situ measurement of furnace dewpoint has not been available, so this method is not used to determine carbon potential.

Another technique of monitoring endothermic gas composition has been measurement of residual oxygen ($O_2$) in the gas, but direct reading of this gas through probes results in a number of problems, including assumptions regarding CO level in the gas, the presence of soot, and catalytic action by the probe itself.

Multiple gas infra-red (IR) detection systems exist, but the IR technique cannot be conducted at furnace temperature. The sample, typically a slip stream from the furnace, is extracted, cooled, filtered and analyzed. By the time it is analyzed, the portion of the endothermic gas with which it is associated has already passed through the heat treating furnace. In addition, the molecular structure of oxygen is such that the species does not have a "signature" frequency for IR analysis, and hence, oxygen content must be inferred. Also, the presence of ammonia in the endothermic gas is known to damage the infrared sensor cells, making this technique unavailable when an endothermic gas for a nitriding operation is being manufactured.

Raman spectroscopy is a technique well known to the analytical chemist. In a classical Raman analysis, a gaseous sample has an incident light beam focused upon a portion of it. Interaction of the incident light with the gas molecules in the beam results in molecular rotations and/or vibrations of gas molecules that are at least diatomic, that is, they comprise at least two atoms joined by a chemical bond. Since Raman spectroscopy acts upon rotations or vibrations involving chemical bonds, the Raman technique is not applicable to monoatomic gases. The rotational or vibrational modes of the diatomic gases yield scattered radiant energy, with much of the scattering occurring within the visible spectrum. The characteristic frequency or wavelength of these emissions may be used to identify the different molecular species present. These frequencies are often referred to as "Raman shifts", because they represent a shift of wavelength or frequency from the incident frequency. In some gases, two shifts may be observed. For example, a rotational shift in $H_2$ is seen at a frequency of 587 $cm^{-1}$, and a vibrational shift is seen at 4156 $cm^{-1}$. In others, only one is observed, or the other possible observed shifts may be so close to those for other gases that they are not sufficiently characteristic. However, all of the gases of particular interest in the endothermic gas have good characteristic Raman shifts: carbon dioxide at 1285 and 1388 $cm^{-1}$; oxygen at 1556 $cm^{-1}$; carbon monoxide at 2143 $cm^{-1}$; nitrogen at 2331 $cm^{-1}$, water at 3657 $cm^{-1}$. When these frequency shifts are applied to a monochromatic wavelength, such as that provided by an argon ion laser having a wavelength of 514.5 nm, for example, it will be seen that the emissions of interest all fall within the visible range. When the laser having a wavelength of 514.5 nm is used, the above gases may be all detected by scanning in the region from 514.5 to 660.0 nm, which represents a range of Raman shifts of from 0 to 4500 $cm^{-1}$. The selection of the particular wavelength of the argon laser light is considered important, because it allows all necessary measurements to be taken at wavelengths under 660 nm. Infrared light is generally defined as starting at about 700 nm, so the spectrum of interest is below the infrared in terms of wavelength. This means that thermally-induced infrared signals will not interfere with the characteristic wavelengths of interest. A laser having an orange or red color would require scanning into the infrared region.

In addition to the argon ion laser, other lasers which are known to be useful in this application include a Nd-Yag laser with an emission wavelength of 532 nm and a solid state diode laser having an emission wavelength of 789 nm. It will be quickly recognized that this latter laser clearly crosses over into the infrared spectrum in its operation, but other properties of the solid state diode laser may provide sufficient advantage to permit its effective use.

Figure 3:
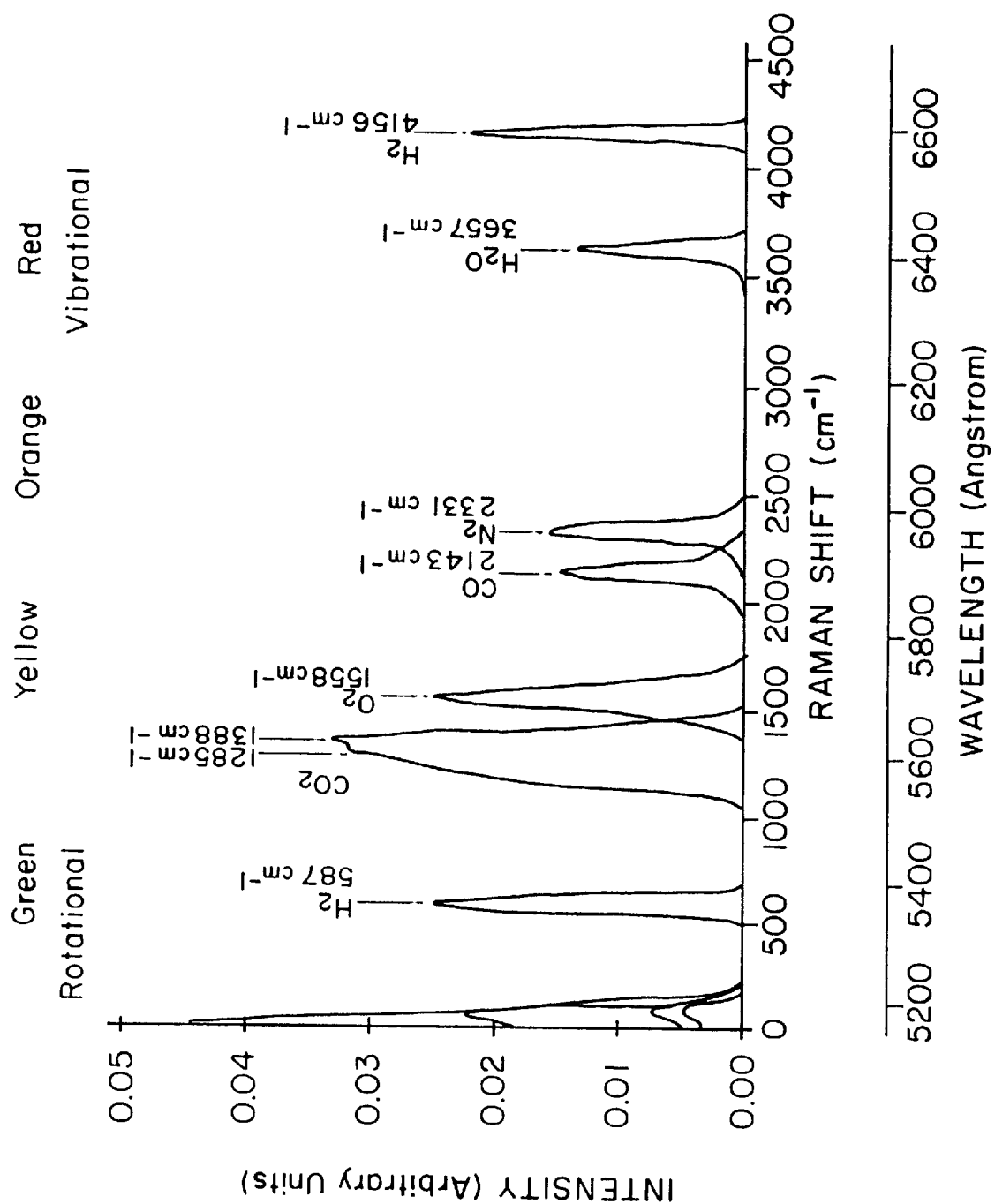
FIG. 3 is a graph of the computed Raman spectrum of the diatomic gas species of interest.

The Raman technique is not so simple that the relative intensities of the scattered light received at each of the characteristic frequencies may be directly compared to determine relative compositions. However, the intensities at a given number density of the gas may be easily determined, when factors such as scattering cross section for the individual molecules are considered. These theoretical values can then be experimentally verified through the testing of known gas samples. A diagram showing these intensities is shown as FIG. 3. With this information in hand, the acquisition of one set of intensity data across the spectral range of interest allows a calculation of the gas composition. The calculation algorithm is easily implemented on readily available computers.

The schematic layout of the present invention is shown in FIG. 1. In the system, a hydrocarbon gas, typically natural gas primarily comprising methane, is supplied from a source 12 through a conduit 14 to a catalytic converter 16. Air or oxygen, but preferably air, is supplied from a source 18 through a conduit 20 into the catalytic converter 16. In the converter 16, the passage of the gases over a heated catalyst bed 22 generates an endogas, which exits the converter 16 through conduit 24, which constitutes a flow chamber and connects with a heat treating furnace 26, where metal products (not shown) are treated by exposure to heat and the endogas. After circulating within the heat treating furnace 26, the endogas is exhausted from the furnace through a conduit 28. This last conduit 28 may lead the gas to a cleanup stage before to atmospheric exhaustion, to direct atmospheric exhaustion, or possibly to some limited recycle back to the converter 16. Of particular interest in the diagram are the three test points 32, 34 and 36 shown in the diagram. Each of the test points comprises a window 38 providing access for light into the conduit. Positioned proximate to each window is a probe 50, as shown in better detail in FIG. 2. Each probe 50 has an input optical fiber 54 and an output optic fiber 66. Each of the input optic fibers 54 is communicated to laser 40 through a multiplexer 42, where laser light originating in the laser is divided by the multiplexer for distribution. Each of the output optic fibers 66 is communicated to a spectral analyzer 44, where light gathered in the respective output optic fibers may be analyzed, as described elsewhere herein.

Figure 2:
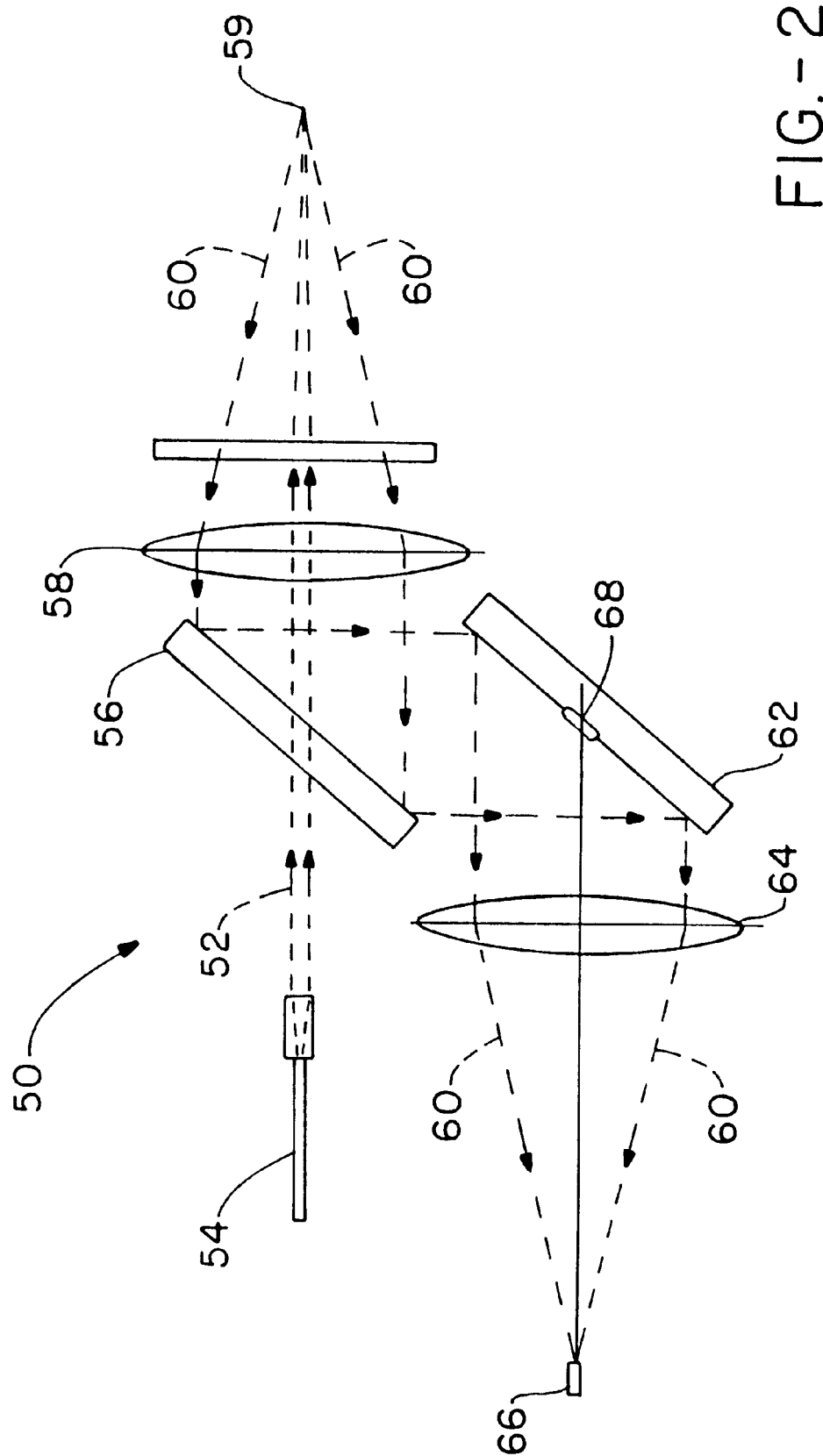
FIG. 2 shows a diagram of the optical configuration of the probe device.

A porthole having the transparent window 38 capable withstanding the high temperatures encountered inside the flow chamber must be provided to allow the incident light to be focused in the flow chamber. A typical window 38 for such a flow chamber will be comprised of quartz, although other materials will be known to one of skill in the art. A test probe will be positioned proximate to the window to inject the incident light into the flow chamber. A typical probe 50 used in this technique is shown in FIG. 2. A beam of monochromatic light 52 is provided to the probe in an optic fiber 54, generally referred to as a delivery fiber. The beam 52 passes through a dichroic mirror 56, through the center of a collection lens 58 and through the window into the flow chamber interior, where the light is focused into a relatively small test volume 59. Scattered light 60 emanating from the test volume 59 receiving the incident light 52 passes through the window and is collected in the collection lens 58. The dichroic mirror 56 and a fully reflecting mirror 62 are aligned so that the scattered light 60 collected strikes a refocusing lens 64, which focuses the light upon a collection fiber 66. The fully reflecting mirror 62 has a mask 68 aligned along the central axis of the refocusing lens 64, so that light passing along that axis does not reach the collection fiber 66. The monochromatic light 52, preferably argon ion laser light, used in the probe should be modulated with an optical chopper (not shown) prior to introduction into the delivery fiber 54. A typical chopping frequency is on the order of 400 Hz. This modulation imparted to the incident light results in a similar modulation to the scattered light captured in the collection fiber. The scattered light 60 captured may be spectrally separated by known means and detected by a photomultiplier tube, which is also well known.

Although the above discussion describes a system in which a single laser provides a single incident beam for use with a single window, the ability to "multiplex" a laser light beam into fiber optic cables for use in a plurality of windows would be within the skill level of one of ordinary skill in this art. In this manner, it is known to be able to monitor the gas composition of the gas in the flow chamber at a variety of points. For example, one may well wish to monitor the gas composition emerging from the catalytic section, along the flow chamber prior to the heat treating furnace and beyond the heat treating furnace. Such multiple point monitoring is useful for recycling the endothermic gas or a portion thereof. In the simplest embodiment of the present invention, a single probe 50 would be located at window 34, but in more complex embodiments, the use of probes 50 at window 32 would permit the collection of composition data on the feed gas and the use of a probe 50 at window 36 would analyze the gas composition exiting the heat treating furnace.

Details for the calibration of a system such as this are provided in a paper by the inventor entitled "Potential New Sensor For Use with Convention Gas Carburizing", which was presented at the 16th ASM Heat Treating Society Conference and Exhibit, Mar. 19–21 1996 in Cincinnati, Ohio. That paper was incorporated into the provisional application 60/037,790 upon which this application is based and is incorporated herein by reference thereto. Once the device as described herein is calibrated for the various diatomic gases to be detected, there are several modes of operation which may be practiced. In a first mode, each and every of the diatomic gases may be detected and the gas analysis calculated. In a second mode, a single diatomic gas may be detected and compared against a baseline gas such as nitrogen. In this second mode, it might be particularly useful to monitor carbon monoxide concentration.

In selecting the specific laser to be used in the above apparatus, it should be kept in mind that the thermal background of the endothermic gas will cause "noise" due to excitation of the gas molecules. As the temperature of the gas increases, the thermal excitation and the emissions from the gas, particularly in the infrared portion of the spectrum, will proportionately increase. If a relatively low power laser is used for the incident beam, the gas sample will necessarily have to be cooled to reduce the IR "noise" and distinguish the emissions due to the Raman scattering. It is, therefore, quite desirable for the laser to be selected with a power level sufficiently high to overcome the thermal noise and provide an easily readable signal even when the gas being detected is in the range of 1000° F. or greater. Other factors requiring increased power in the laser from those employed in known Raman spectroscopic techniques are the need for a higher ratio of signal to noise and inherent power losses in transmission of the laser beam through the fiber optic cables. The minimum power believed to be effective in this application is about 1 watt and the normal operating range would be expected to be in the range of about 1 to about 5 watts.

Once the above principles are applied to obtain and monitor the concentrations of the various diatomic gases present in the feed gases to the catalytic conversion section and in the product endothermic gas of interest, it will of course be within the skill of one of ordinary skill in the art of process control to apply feedback principles to control the operation of the catalytic process, thereby providing an endothermic gas mixture of stable concentration to the heat treating furnace. Also, the ability to obtain concentration information on the gas effluent from the heat treatment section will permit, in a proper situation, the recycling of these effluent gases or portions thereof.

Although the present invention has been described above in detail, the same is by way of illustration and example only and is not to be taken as a limitation on the present invention. Accordingly, the scope and content of the present invention are to be defined only by the terms of the appended claims.

What is claimed is:

1. A method for sensing at least one diatomic gas in a flow chamber, comprising the steps of:

a) providing the flow chamber with a window transparent to light in the visible spectrum;

b) focusing an incident beam from a monochromatic light source on the gas at a focal point internal to the flow chamber through the window, wherein a temperature of the gas measured at the focal point is in excess of 250° F.;

c) collecting a scattered light beam from the flow chamber passing external to the flow chamber through the window; and d) analyzing the intensity of the collected scattered beam in at least one characteristic frequency for each of the at least one diatomic gases.

2. The method of claim 1 wherein the incident beam is brought proximate to the window in a first fiber optic cable.

3. The method of claim 2 wherein the scattered beam is collected proximate to the window in a second fiber optic cable.

4. The method of claim 1 wherein the temperature at the focal point of the incident beam is in excess of 1000° F.

5. The method of claim 4 wherein the at least one diatomic gas being sensed is a mixture comprising carbon monoxide, hydrogen and nitrogen.

6. The method of claim 4 wherein the incident beam is brought proximate to the window in a first fiber optic cable.

7. The method of claim 6 wherein the scattered beam is collected proximate to the window in a second fiber optic cable.

8. The method of claim 4 wherein the monochromatic light source is an argon ion laser.

9. The method of claim 8 wherein the argon ion laser emits lights at a wavelength of 514.5 nm.

10. The method of claim 9 wherein the argon ion laser has a power of at least about 1 watt.

11. The method of claim 1 wherein the monochromatic light source is an argon ion laser.

12. The method of claim 11 wherein the argon ion laser emits lights at a wavelength of 514.5 nm.

13. The method of claim 11 wherein the argon ion laser has a power of at least about 1 watt.

14. The method of claim 1 wherein the at least one diatomic gas being sensed is a mixture comprising carbon monoxide, hydrogen and nitrogen.

* * * * *